United States Patent
Fatemi et al.

(10) Patent No.: US 6,511,429 B1
(45) Date of Patent: Jan. 28, 2003

(54) ULTRASONIC METHODS AND SYSTEMS FOR REDUCING FETAL STIMULATION

(75) Inventors: Mostafa Fatemi; James F. Greenleaf, both of Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 33 days.

(21) Appl. No.: 09/640,578

(22) Filed: Aug. 17, 2000

(51) Int. Cl.$^7$ .................................................. A61B 8/00
(52) U.S. Cl. ...................................... 600/443; 600/437
(58) Field of Search ................................. 600/443, 447, 600/437, 462, 304, 500, 485, 458

(56) References Cited

U.S. PATENT DOCUMENTS

| | | | |
|---|---|---|---|
| 4,217,684 A | 8/1980 | Brisken et al. | 29/25.35 |
| 4,425,525 A | 1/1984 | Smith et al. | 310/336 |
| 4,441,503 A | 4/1984 | O'Donnell | 128/660 |
| 4,470,305 A | 9/1984 | O'Donnell | 73/626 |
| 4,569,231 A | 2/1986 | Carnes et al. | 73/626 |
| 5,606,155 A | 2/1997 | Chalana et al. | 128/660.07 |
| 5,935,061 A * | 8/1999 | Acker et al. | 600/304 |
| 6,093,151 A * | 7/2000 | Shine et al. | 600/485 |
| 6,245,025 B1 * | 6/2001 | Torok et al. | 600/500 |

OTHER PUBLICATIONS

Ultrasound–Stimulated Vibro–Acoustic Spectrography, Science vol. 280, Apr. 3, 1998, Fatemi, et al.
Modeling and Measurements of Audio Sound Produced by Obstetric Ultrasound, 7$^{th}$ World Congress on Ultrasound in Obstetrics and Gynecology, Oct. 1997, A5, Fatemi, et al.

* cited by examiner

Primary Examiner—Francis J. Jaworski
Assistant Examiner—Maulin Patel
(74) Attorney, Agent, or Firm—Quarles & Brady LLP

(57) ABSTRACT

The operation of an ultrasonic imaging system may be altered to reduce the generation of audible sound that can stimulate a fetus. A number of altered modes of operation are possible including the reduction of ultrasonic pulse peak power and the changing of the pulse repetition rate to a frequency outside the audible range. The change in operation may be manually selected, or conditions for fetal stimulation may be detected and a mode change made automatically.

12 Claims, 2 Drawing Sheets

ULTRASONIC METHODS AND SYSTEMS FOR REDUCING FETAL STIMULATION

BACKGROUND OF THE INVENTION

The field of the invention is coherent imaging using vibratory energy, such as ultrasound and, in particular, ultrasound imaging of a fetus.

There are a number of modes in which ultrasound can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode).

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed.

In the so-called C-scan method, the transducer is scanned across a plane above the object as it produces a series of ultrasonic pulses. Only the echoes reflecting from the focal depth of the transducer are recorded. The sweep of the electron beam of a CRT display is synchronized to the scanning of the transducer so that the x and y coordinates of the transducer correspond to the x and y coordinates of the image.

Ultrasonic transducers for medical applications are constructed from one or more piezoelectric elements sandwiched between a pair of electrodes. Such piezoelectric elements are typically constructed of lead zirconate titanate (PZT), polyvinylidene diflouride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231.

When used for ultrasound imaging, the transducer typically has a number of piezoelectric elements arranged in an array and driven with separate voltages (apodizing). By controlling the time delay (or phase) and amplitude of the applied voltages, the ultrasonic pulses produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the signal pulses from each transducer array element.

All these modes of ultrasonic imaging rely on the production of short pulses of ultrasonic energy. Each transmitted ultrasonic pulse and the resulting echo is a measurement which is repeated rapidly during a scan to acquire sufficient data for an image.

Obstetricians rely heavily on observations obtained by ultrasound imaging to study normal and abnormal fetal behaviors. Ultrasound is not audible to humans since it is typically in the 2 MHz to 10 MHz frequency range, well above the 20 kHz upper limit of human hearing. As a result, it is assumed that ultrasonic imaging is not disruptive and is a relatively benign imaging modality to employ when evaluating fetal behavior. Stimulation of the fetus is detrimental in at least two situations where ultrasonic imagers are used. Stimulation of the fetus may introduce errors in fetal evaluation tests, such as biophysical profile tests or fetal hearing evaluation studies. Fetal motions can also complicate the performance of delicate invasive procedures in which fetus immobility is critical.

SUMMARY OF THE INVENTION

The present invention arises from the discovery that pulsed ultrasonic imaging systems produce audible sounds which stimulate a fetus. A radiation force is produced by ultrasonic waves reflecting off an object and that force is modulated in amplitude at the pulse repetition rate of the ultrasound system. This produces audible sound that stimulates the fetus when it reaches a certain level. The present invention is an ultrasound imaging system which operates in such manner as to avoid fetal stimulation, and which signals the operator when operating conditions exist that may stimulate the fetus.

One aspect of the present invention is to provide an ultrasound imaging system in which the pulse repetition rate is outside the audible frequency range. This is achieved using either a continuous wave (CW) imaging method or a pulse repetition rate that is above audible frequencies.

Another aspect of the invention is to reduce the peak power of ultrasonic pulses such that any audible sounds produced by them will be below the level which stimulates the fetus. This may be achieved without significantly reducing the signal-to-noise ratio of the acquired image data by shaping each pulse to spread the power in time such that its peak power can be reduced. To maintain the resolution of the image acquired with such shaped pulses, a matched filter is used in the receiver to restore axial image resolution.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

Figure 1:
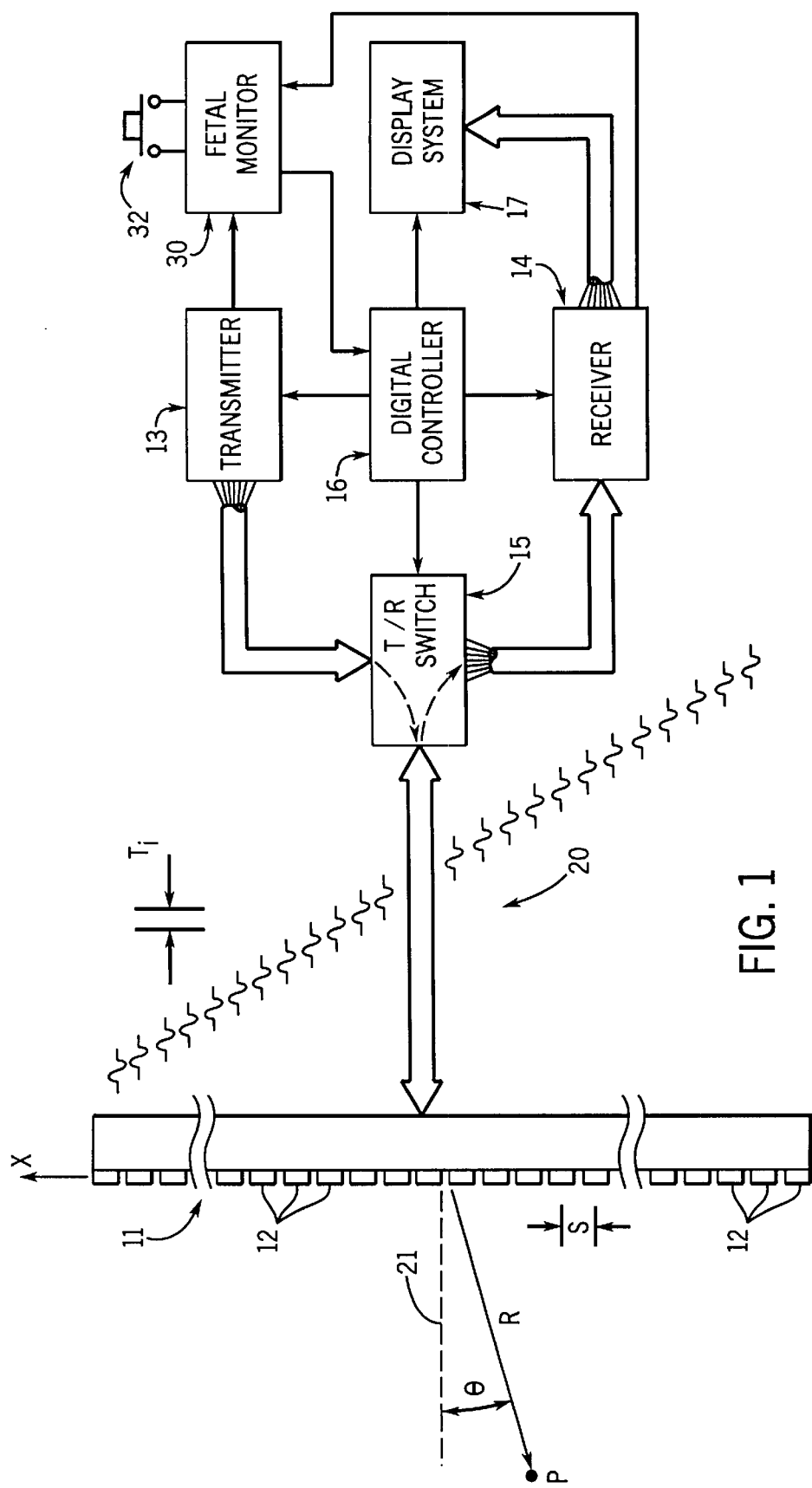
FIG. 1 is a block diagram of an ultrasonic imaging system which employs the present invention.

Medical ultrasound literature often states that ultrasound is not audible to humans. Although this is true based on the mechanism of human hearing system and linear acoustic theory, it can mislead one to conclude that diagnostic ultrasound would not generate audible acoustic energy in the human body.

An ultrasound beam can exert a steady force on an object that absorbs or reflects the beam. The so called "radiation force" is a second order acoustic phenomenon which results from changes in energy density of the ultrasound produced by the object. Radiation force magnitude (f) is proportional to the average energy density of the incident wave (<E>), the projected area (S) and a factor ($d_r$) that represents the reflection and absorption properties of the object:

$$F=d_r S<E>.$$

Higher reflection coefficients result in a larger force. Hence, a highly reflecting object such as a bone in soft tissue, will experience a larger force than a moderately reflecting object such as fat.

Cyclic variations in the amplitude of the impinging ultrasound beam result in a vibrating force on the object which, in turn, produces periodic elastic waves in the object and a secondary acoustic field in the surrounding medium. Continuous wave (CW) ultrasound with a constant amplitude, on the other hand, can only produce a steady force but no acoustic waves.

Diagnostic ultrasound scanners transmit high energy bursts of ultrasound energy into a body at the pulse repetition frequency of the system. These bursts are absorbed or reflected by tissues in the beam path. Hence, they produce a periodic radiation force and an acoustic field in the body at the pulse repetition frequency which is usually in the audible range (<20 kHz).

A main difference between the ultrasound generated sound and the sound from a conventional source is the energy concentration pattern. If a conventional sound source, such as an obstetric vibro-acoustic device (artificial larynx), is used to transmit sound into the body, the sound energy spreads and diffuses as it travels in tissue layers. But the sound from the radiation force produced by a pulsed ultrasound system does not originate from the transducer surface, rather it is generated internally and mostly on the object located at the focal area of the beam. It is at this region where the ultrasound energy is concentrated and is converted to audio frequency elastic waves due to the radiation force. Hence there is no attenuation by diffusion, and the focal region acts as a virtual sound source inside the body. For instance, if an obstetric examination of the fetal head is in the focal region, the sound will be produced on any calcified bone like the ossicle structure of the ear. This mechanism is significantly different from the natural way sound travels to the fetus. The fetal cochlea is not very sensitive to the sound traveling through the body because particle displacement on both sides of the eardrum is much less than in air, and because the sound acts with equal pressures on the oval and round windows. In contrast, pulsed ultrasound can generate sound directly within the fetal head, which can be conducted to the cochlea more efficiently, especially if the malleus, incus, or stapes are targeted by the ultrasound beam. These bones are ossified in the fourth month of gestation, and hence will be highly reflective and likely to receive a stronger radiation force. Any resulting ossicle movement acts directly on the oval window but not on the round window. Therefore, the vibration is efficiently conducted on the fetal cochlea. Ultrasound pulses may also stimulate fetal auditory nerves directly. Such an effect has been detected by direct observation of the electrical activity of midbrain centers.

Continuous Waveform Method

One method to avoid producing audible sounds is to transmit ultrasound energy in the form of continuous waveform rather than pulses. In exchange, the instantaneous power can be reduced to a very low level. In this method there is no pulse. Ultrasound energy is transmitted to the patient body continuously. Hence, there is no audible impact of energy, and therefore no sound is generated.

In order to delineate reflections from different scatterers along the beam path, the continuous waveform is designed to have a particular time dependency. The receiver is also designed to optimally detect this time dependency. For this purpose, one of the known optimal signal design and detection methods can be used. The signal does not have to be infinite in duration, but can be long enough such that the effect of energy impact on the body (or the fetus) is spread in time and is negligible.

An example of a suitable continuous waveform is a chirp waveform, which is known in the radar community. Here, a sinusoidal waveform with time varying frequency is used to drive the transducer. The receiver detects the returned signal and extracts spatial information of the scatterers using known correlation, matched filter, or similar methods.

Another example of a suitable continuous waveform is to use a pseudorandom (noise like) signal to modulate the frequency or the phase of a sinusoidal carrier waveform. The receiver is matched to the pseudorandom pattern and detects the scatterer using known correlation or similar methods.

These are only examples of the novel approach based on spreading the energy of ultrasound in time for the purpose of reducing the sound power generated by ultrasound emission to the body.

Frequency Methods

These methods alter the frequency spectrum of the sound produced by a pulsed ultrasound system.

Method I—Increased pulse repetition at single frequency

Normally, clinical scanners produce ultrasound pulses at a few kilo Hertz (kHz) repetition rate. This is in the audible range of human hearing. In this method the pulse repetition rate of the scanner is changed to a level higher than 15 kHz, which is the typical hearing upper limit for a human fetus. This threshold is an example, and other threshold values can also be used for this purpose.

Method II—Increased pulse repetition at multiple frequencies

A drawback of Method I above, is that when the pulse repetition frequency (PRF) of a scanner is increased the depth of view is decreased. This is because the time interval between two consecutive pulses is not long enough to collect echoes coming from the deep areas of the body. An alternative method is to transmit ultrasound pulses at a high PRF as in Method I, but produce the pulses at different ultrasound carrier frequencies. The receiving transducer is designed to only receive echo signals from one of the transmitted carrier frequencies. Those pulses that are transmitted at a different frequency are not detected by the receiver. In this method the repetition frequency is high so the sound made by n successive pulses in the patient body is beyond human hearing frequency range. However, the imaging part of the system operates at a lower PRF, which is 1/n times less than the actual PRF.

Figure 2:
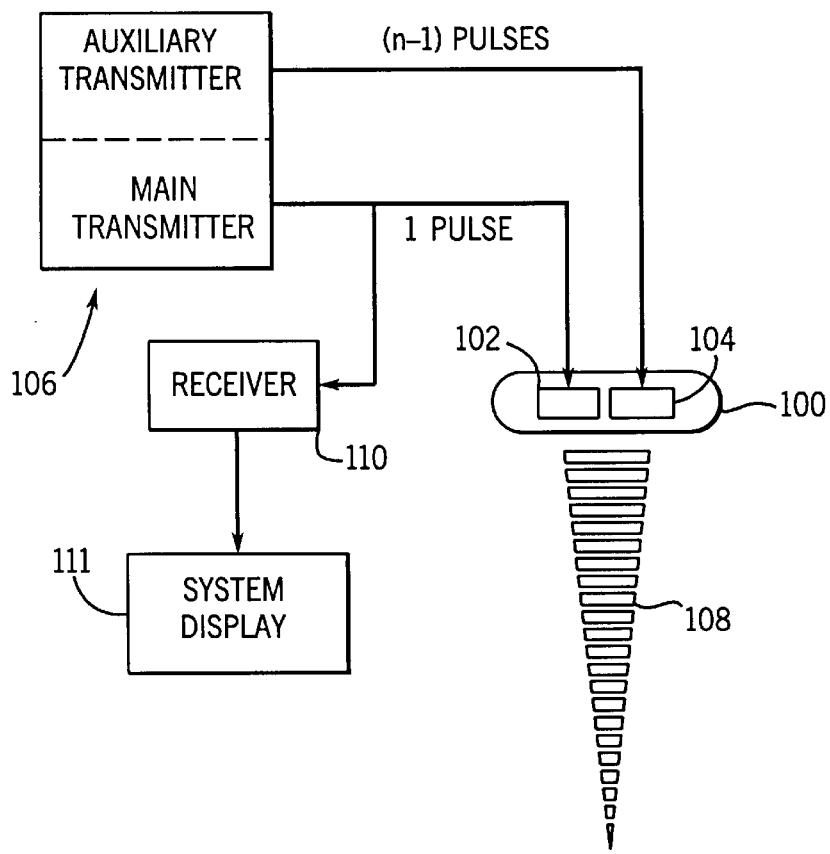
FIG. 2 is a block diagram illustrating one embodiment of the invention in an ultrasonic imaging system.

As illustrated in FIG. 2, to practice this method, an ultrasound transducer 100 has elements which operate at two ultrasound carrier frequencies. The group of elements that operate at the desired imaging frequency (e.g. 2.5 MHz) are the MAIN elements 102, and the corresponding frequency is called the MAIN FREQUENCY. The other group of elements are called AUXILIARY elements 104 and their corresponding carrier frequency (e.g. 6 MHz) is called the AUXILIARY FREQUENCY. The pulse generator 106 produces pulses at a high pulse repetition frequency (PRF), for example at 15 kHz. Every n-th pulse is directed to the main transducer elements 102, and the remaining pulses are directed to the auxiliary transducer elements 104. Therefore the transducer 100 produces ultrasound pulses at two frequencies, only 1/n of which are at the main frequency. Beams 108 from both sets of elements are steered and focused to the same positions.

A receiver 110 is designed to receive only the echoes produce by the main transducer 102 at the main frequency and reconstruct an image on display 111. Therefore, the scanner can image at a PRF that is equal to 1/n of the actual PRF of the ultrasound pulses sent into the subject.

Reduced Power Method

Conventional ultrasound imaging systems produce pulses with peak power intensities of hundreds of watts per square centimeter. These high power intensity pulses produce audible "clicks" at the beam focus site. The strategy underlying this method is to reduce the peak power produced by the pulses without substantially reducing image quality. Reduced peak power results in a corresponding reduced audible sound level, and if reduced sufficiently, the fetus is not stimulated.

The sound generated by the ultrasound pulses is proportional to the ultrasound power. In conventional scanners, the ultrasound energy is produced in very short pulses. Hence the instantaneous power of these pulses is very high. To reduce the instantaneous power but not the total energy, the pulse energy may be spread in time. We call this method Waveform Optimization. However, when the ultrasound pulse is stretched in time, the axial resolution of the imaging system decreases accordingly. To prevent loss of resolution, a particular pulse shape (for example a Gaussian bell shape) is produced. Its total energy is substantially the same as a conventional ultrasound pulse, but its time duration is much greater and its peak instantaneous energy is much smaller than that of a conventional ultrasound pulse.

Figure 3:
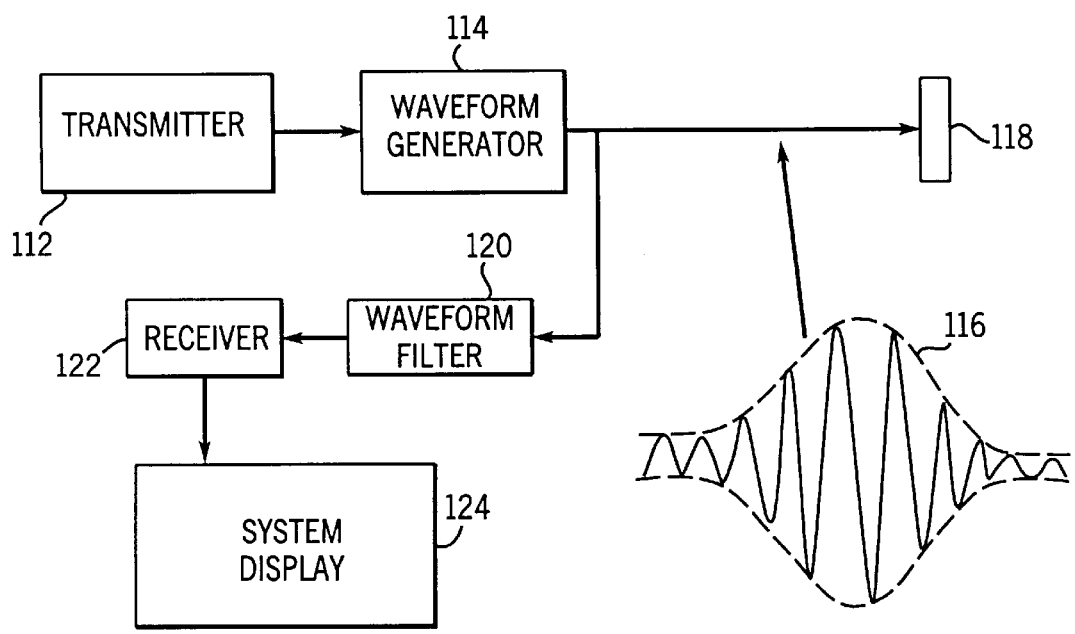
FIG. 3 is a block diagram illustrating a second embodiment of the invention in an ultrasonic imaging system.

As shown in FIG. 3, an ultrasound imaging system which implements this method includes a transmitter 112 that produces a pulse at the carrier frequency. This pulse is shaped by a waveform generator 114 to form a Gaussian bell shape 116 and it is then applied to a transducer 118. The reflected echoes are received by the transducer 118 and applied to a matched waveform filter 120 that compresses the received echo to a very short pulse that is input to a receiver 122 and processed to produce an image on display 124. The peak power of the shaped pulses is thus substantially reduced while maintaining the axial resolution of the imaging system.

DESCRIPTION OF THE PREFERRED EMBODIMENT

Referring particularly to FIG. 1, an ultrasonic imaging system includes a transducer array 11 comprised of a plurality of separately driven elements 12 which each produce a burst of ultrasonic energy when energized by a pulse produced by a transmitter 13. The ultrasonic energy reflected back to the transducer array 11 from the subject under study is converted to an electrical signal by each transducer element 12 and applied separately to a receiver 14 through a set of switches 15. The transmitter 13, receiver 14 and the switches 15 are operated under the control of a digital controller 16 responsive to the commands input by the human operator. A complete scan is performed by acquiring a series of echoes in which the switches 15 are set to their transmit position, the transmitter 13 is gated on momentarily to energize each transducer element 12, the switches 15 are then set to their receive position, and the subsequent echo signals produced by each transducer element 12 are applied to the receiver 14. The separate echo signals from each transducer element 12 are combined in the receiver 14 to produce a single echo signal which is employed to produce a line in an image on a display system 17.

The transmitter 13 drives the transducer array 11 such that the ultrasonic energy produced is directed, or steered, in a beam. A B-scan can therefore be performed by moving this beam through a set of angles from point-to-point rather than physically moving the transducer array 11. To accomplish this the transmitter 13 imparts a time delay ($T_i$) to the respective pulses 20 that are applied to successive transducer elements 12. If the time delay is zero ($T_i$=0), all the transducer elements 12 are energized simultaneously and the resulting ultrasonic beam is directed along an axis 21 normal to the transducer face and originating from the center of the transducer array 11. As the time delay ($T_i$) is increased as illustrated in FIG. 1, the ultrasonic beam is directed downward from the central axis 21 by an angle θ. The relationship between the time delay increment $T_i$ added successively to each $i^{th}$ signal from one end of the transducer array (i=1) to the other end (i=n) is given by the following relationship:

$$T_i = (i-(n-1)/2)d \sin \theta/c + (i-(n-1)/2)^2 \, d^2 \cos^2\theta / 2R_T c + T_o \quad (1)$$

where d=equal spacing between centers of adjacent transducer elements 12, c=the velocity of sound in the object under study.

RT=range at which transmit beam is to be focused.

$T_o$=delay offset which insures that all calculated values ($T_i$) are positive values.

The first term in this expression steers the beam in the desired angle θ, and the second is employed when the transmitted beam is to be focused at a fixed range. A sector scan is performed by progressively changing the time delays $T_i$ in successive excitations. The angle θ is thus changed in increments to steer the transmitted beam in a succession of directions. When the direction of the beam is above the central axis 21, the timing of the pulses 20 is reversed, but the formula of equation (1) still applies.

Referring still to FIG. 1, the echo signals produced by each burst of ultrasonic energy emanate from reflecting objects located at successive positions (R) along the ultrasonic beam. These are sensed separately by each segment 12 of the transducer array 11 and a sample of the magnitude of the echo signal at a particular point in time represents the amount of reflection occurring at a specific range (R). Due to the differences in the propagation paths between a focal point P and each transducer element 12, however, these echo signals will not occur simultaneously and their amplitudes will not be equal. The function of the receiver 14 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle θ.

To simultaneously sum the electrical signals produced by the echoes from each transducer element 12, time delays are introduced into each separate transducer element channel of the receiver 14. In the case of the linear array 11, the delay introduced in each channel may be divided into two components, one component is referred to as a beam steering time delay, and the other component is referred to as a beam focusing time delay. The beam steering and beam focusing time delays for reception are precisely the same delays ($T_i$) as the transmission delays described above. However, the focusing time delay component introduced into each receiver channel is continuously changing during reception of the echo to provide dynamic focusing of the received beam at the range R from which the echo signal emanates. This dynamic focusing delay component is as follows:

$$T_k = (k-(n-1)/2)2 \; d^2 \cos^2 \theta / 2Rc \qquad (2)$$

R=the range of the focal point P from the center of the array 11;

$T_k$=the desired time delay associated with the echo signal from the $k^{th}$ element to coherently sum it with the other echo signals.

Under the direction of the digital controller 16, the receiver 14 provides delays during the scan such that the steering of the receiver 14 tracks with the direction of the beam steered by the transmitter 13 and it samples the echo signals at a succession of ranges and provides the proper delays to dynamically focus at points P along the beam. Thus, each emission of an ultrasonic pulse results in the acquisition of a series of data points which represent the amount of reflected sound from a corresponding series of points P located along the ultrasonic beam.

The display system 17 receives the series of data points produced by the receiver 14 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display.

The ultrasound system may operate in a number of well-known modes to produce different types of images. The preferred embodiment of the present invention is an improvement to the imaging system in which its mode of operation is altered to reduce the probability of stimulating a fetus which comes into the field of view of the imager.

A fetal monitor circuit 30 couples to the digital controller 16 and is operable to change the operation of the imaging system as will be described in more detail below. The fetal monitor 30 is responsive to the operation of a manually operable switch 32 to make the mode change, or circumstances can be detected by the fetal monitor 30 which cause the mode change to occur automatically.

One of the functions of the fetal monitor circuit 30 is to produce an alarm to warn or inform the operator that conditions exist for stimulating the fetus. This warning can be in any form, such as a written, audio or visual message. The alarm may also prevent some functions of the scanner. For example, it may automatically reduce the power output to prevent accidental stimulation of the fetus.

The alarm may be operated in a number of ways. Selecting a "fetal mode" of operation will produce a warning message and automatically reduce power output. On the other hand, the alarm may be triggered by detecting a set of conditions which may result in fetal stimulation. To detect these conditions. The ultrasound signal received by the receiver 14 or the video image which it produces is analyzed to detect the existence of the fetal skull or other organs in the imager field of view. This event alone may trigger an alarm message to the operator, or it may trigger a second detection step. The second detection step examines the pulse repetition rate and the output power produced by the transmitter 13. If the pulse repetition rate is within the fetal audible range and the transmit power is higher than a fetal stimulation threshold level, the alarm message is produced.

The operator can manually alter the mode of system operation to avoid fetal stimulation, or the system may automatically change mode of operation in response to a detected alarm condition. The system may change its mode of operation to practice either of the methods described above with reference to FIGS. 2 and 3.

The imaging system of FIG. 1 is adapted to practice the method described above with respect to FIG. 2 by adding an auxiliary transducer and auxiliary transmitter to the system. These added elements are substantially the same as the main transducer 11 and transmitter 13 except they operate at a substantially different carrier frequency. For example, the main transducer 11 and transmitter 13 operate at 2.5 MHz and the auxiliary elements operate at 6 MHz. The digital controller 16 operates the two transmitters as described above to produce one pulse with main transmitter 13 and transducer 11 for every n−1 pulses produced by the auxiliary elements. The pulse repetition rate of the combined main and auxiliary transmitters is above the audible frequency range (e.g. 15 kHz) and the number of pulses n is selected such that the pulse repetition rate of the main transmitter 13 produces the specified image quality.

The imaging system of FIG. 1 is adapted to practice the method described above with respect to FIG. 3, by adding a waveform generator to the output of transmitter 13 and a matched, waveform filter to the input of receiver 14. As described above, the waveform generator re-shapes each pulse produced by the transmitter 13 such that it has a longer duration and lower peak power. The waveform filter is matched to the particular shape of this pulse (e.g. Gaussian bell shape) such that the received echo signals are compressed to short duration signals prior to application to the dynamic focusing elements of the receiver 14.

What is claimed is:

1. In an ultrasonic imaging system having a transmitter and a transducer for producing an ultrasonic beam in a subject and a receiver for producing an image from received echo signals, the improvement comprising:

a fetal monitor for indicating that the subject includes a human fetus; and means for altering the operation of the ultrasonic imaging system when a human fetus is imaged to inhibit the ultrasonic imaging system from producing audible sounds in the fetus of sufficient magnitude to stimulate the fetus.

2. The improvement as recited in claim 1 in which the means for altering the operation limits the peak power of ultrasonic pulses produced by the transducer to form the ultrasonic beam.

3. The improvement as recited in claim 2 in which the means for limiting peak power of the ultrasonic pulses includes a waveform generator which alters the shape of each ultrasonic pulse.

4. The improvement as recited in claim 3 in which the altered shape of the ultrasonic pulses output by the waveform generator maintains total pulse power substantially the same, but reduces pulse peak power.

5. The improvement as recited in claim 4 which includes a waveform filter connected to alter the shape of received echo signals prior to processing by the receiver, the waveform filter being matched with the waveform generator.

6. The improvement as recited in claim 1 in which the means for altering the operation of the ultrasonic imaging system includes means for changing the repetition frequency of ultrasonic pulses produced by the transducer to form the ultrasonic beam.

7. The improvement as recited in claim 6 in which the pulse repetition frequency is changed to a frequency outside the audible range of the fetus.

8. The improvement as recited in claim 6 in which the pulse repetition frequency is changed to a frequency above the audible range of the fetus and only one out of each n received echo signals are used to produce an image.

9. The improvement as recited in claim 8 in which includes auxiliary transducer means for producing auxiliary ultrasonic pulses at an ultrasonic frequency different from the ultrasonic frequency of ultrasonic pulses produced by the transducer, and wherein the auxiliary transducer means produces n−1 ultrasonic pulses out of each n ultrasonic pulses that form the ultrasonic beam.

10. The improvement as recited in claim 1 in which the fetal monitor includes a manually operable device.

11. The improvement as recited in claim 1 in which the fetal monitor includes means for analyzing an image produced by the receiver to detect the presence of a predetermined structure in the image.

12. The improvement as recited in claim 1 in which the fetal monitor includes means for producing an indication to an operator that fetal stimulation by the ultrasonic beam may occur.

* * * * *